United States Patent [19]

Vogel et al.

[11] Patent Number: 4,957,110

[45] Date of Patent: Sep. 18, 1990

[54] STEERABLE GUIDEWIRE HAVING ELECTRODES FOR MEASURING VESSEL CROSS-SECTION AND BLOOD FLOW

[75] Inventors: Robert A. Vogel, Lutherville, Md.; William A. Berthiaume, Hudson; Thomas J. Palermo, Methuen, both of Mass.

[73] Assignee: C. R. Bard, Inc., Murray Hill, N.J.

[21] Appl. No.: 325,223

[22] Filed: Mar. 17, 1989

[51] Int. Cl.⁵ .................... A61B 5/04; A61B 5/026
[52] U.S. Cl. ............................. 128/642; 128/692; 128/693; 128/772
[58] Field of Search ............... 128/642, 692, 693, 772, 128/784, 786

[56] References Cited

U.S. PATENT DOCUMENTS

| | | | |
|---|---|---|---|
| 3,730,171 | 5/1973 | Namon | 128/2.05 Z |
| 3,742,936 | 7/1973 | Blanie et al. | 128/2.1 Z |
| 3,773,037 | 11/1973 | Kolin | 128/2.05 F |
| 3,882,851 | 5/1975 | Sigworth | 128/2.1 Z |
| 3,896,373 | 7/1975 | Zelby | 324/57 R |
| 4,176,662 | 12/1979 | Frazer | 128/6 |
| 4,236,525 | 12/1980 | Sluetz et al. | 128/786 X |
| 4,380,237 | 4/1983 | Newbower | 128/693 |
| 4,401,127 | 8/1983 | Littleford | 128/786 |
| 4,481,953 | 11/1984 | Gold et al. | 128/786 |
| 4,545,390 | 10/1985 | Leary | 128/772 |
| 4,552,127 | 11/1985 | Schiff | 128/1 D |
| 4,559,951 | 12/1985 | Dahl et al. | 128/642 |
| 4,587,975 | 5/1986 | Salo et al. | 128/693 |
| 4,643,202 | 2/1987 | Roche | 128/786 |
| 4,660,571 | 4/1987 | Hess et al. | 128/784 |
| 4,674,518 | 6/1987 | Salo | 128/695 |
| 4,677,990 | 7/1987 | Neubauer | 128/786 |
| 4,699,157 | 10/1987 | Shonk | 128/786 |
| 4,729,384 | 3/1988 | Bazenet | 128/691 |

FOREIGN PATENT DOCUMENTS

| | | | |
|---|---|---|---|
| 3120012 | 2/1983 | Fed. Rep. of Germany | 128/772 |
| 411842 | 9/1974 | U.S.S.R. | 128/693 |

Primary Examiner—Lee S. Cohen
Attorney, Agent, or Firm—Wolf, Greenfield & Sacks

[57] ABSTRACT

A small diameter steerable guidewire that is used to guide a catheter in transluminal coronary angioplasty is provided with a pair of electrodes for measuring the cross-sectional area of a blood vessel and for measuring blood flow. The guidewire includes a shaft and a tip attached to the distal end of the shaft. The shaft is torsionally rigid along its length and includes a conductive tube and a wire extending through the tube. The tip, which can be bent to a prescribed curve when relaxed, is sufficiently flexible to adapt to and follow the contours of a blood vessel. The tip includes a tapered extension of the wire in the shaft. A proximal electrode and a distal electrode are coaxially mounted on the tapered wire and are electrically connected to the tube and the wire, respectively. The electrodes are axially spaced apart by a predetermined distance. Each electrode is preferably a conductive, helically-wound spring. The outside diameter of the steerable guidewire preferably does not exceed about 0.020-inch for coronary use.

40 Claims, 2 Drawing Sheets

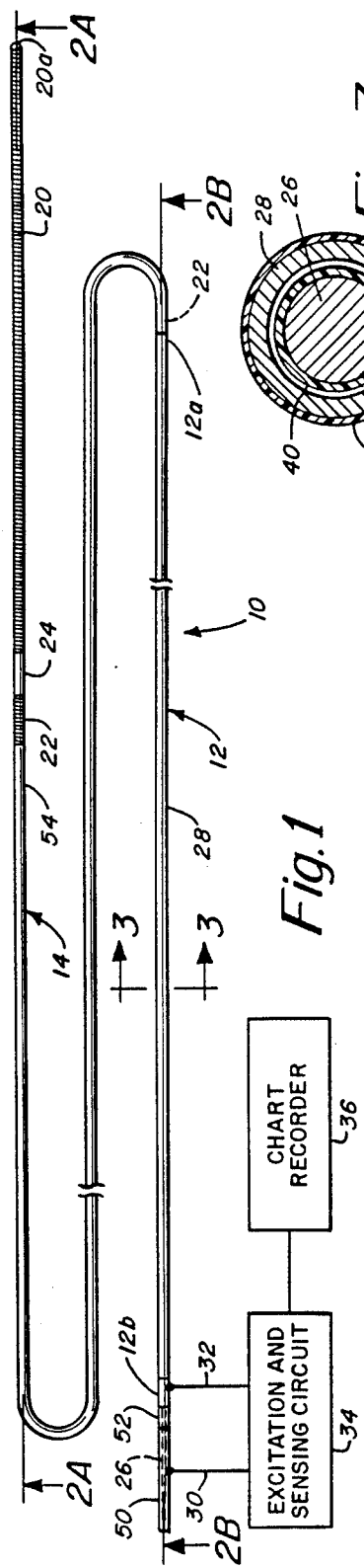
Fig.1
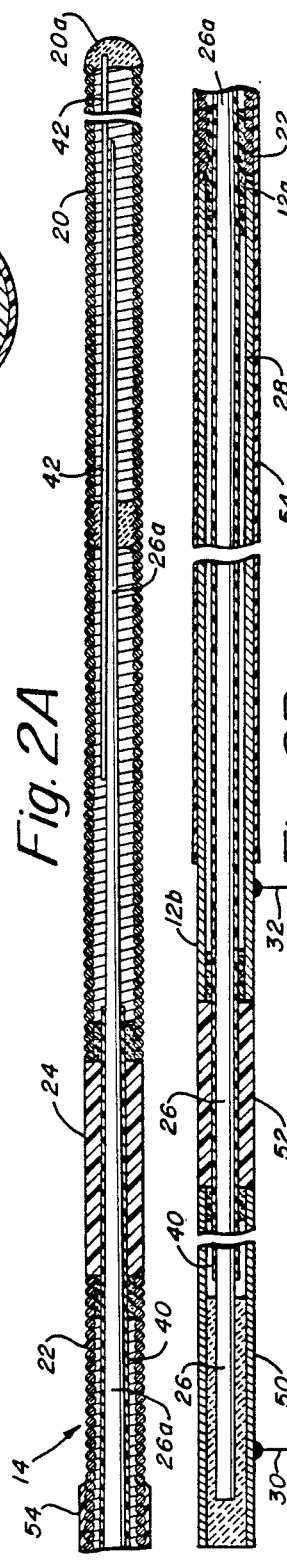
Fig.2A
Fig.2B
Fig.3
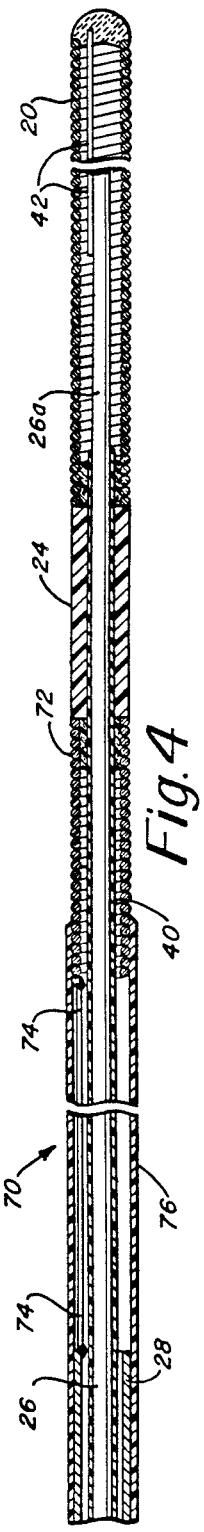
Fig.4

STEERABLE GUIDEWIRE HAVING ELECTRODES FOR MEASURING VESSEL CROSS-SECTION AND BLOOD FLOW

FIELD OF THE INVENTION

This invention relates to a steerable guidewire that is used to guide a catheter in transluminal coronary angioplasty and, more particularly, to a small diameter, steerable guidewire that is provided with a pair of electrodes for measuring vessel cross-section and coronary blood flow.

BACKGROUND OF THE INVENTION

Transluminal coronary angioplasty involves the nonsurgical widening of a passage through an artery that has been narrowed or stenosed by deposits of plaque or plaque-ridden tissue. In one widely used approach, an inflatable balloon mounted on a catheter enlarges the passage through the deposit. In other known approaches the deposit is vaporized with laser energy transmitted through a catheter, or a passage is enlarged by plowing through the deposit with a hot tip device mounted at the distal end of a catheter. Regardless of the technique used for widening the passage through the obstruction, it is desirable for the cardiologist to measure the vessel cross-section before and after the angioplasty procedure in order to evaluate its effectiveness.

A device for measuring the cross sectional area of a blood vessel is disclosed in U.S. Pat. No. 3,896,373 issued July 22, 1975 to Zelby. Two electrodes that are spaced apart by a predetermined distance are secured to the outer surface of a catheter tube, and conductors extend from the electrodes through the tube to the proximal end of the catheter. The catheter carrying the electrodes is advanced through the blood vessel to a measurement site, and an AC voltage is applied to the electrodes. The voltage drop across the electrodes is indicative of the cross-sectional area of the blood vessel between the electrodes, since the applied voltage produces a current through the blood in the vessel.

In order to use the Zelby device in conjunction with an angioplasty procedure, the device is first advanced to the site of the obstruction to perform a measurement of vessel cross-section. Then the measurement device is withdrawn, and the balloon catheter is advanced to the obstructed site in order to perform the dilatation. Then the balloon catheter is withdrawn, and the measurement device is again advanced to the site to perform a second measurement of vessel cross-section. Since both the measurement device and the dilatation catheter can be difficult to advance to the obstructed site, the entire procedure is time consuming and is traumatic to the patient.

A dimension-sensitive angioplasty catheter having an inflatable balloon and a plurality of vessel-measuring electrodes near its distal end is disclosed in U.S. Pat. No. 4,587,985 issued May 13, 1986 to Salo et al. Each of the electrodes is mounted on the surface of the catheter tube and is individually connected to the proximal end of the catheter. One pair of electrodes is selected for connection to the output of an oscillator, and a second pair of electrodes is selected for sensing a signal that results from conduction through the blood in the vessel. While the Salo et al catheter avoids the problem of separate devices for vessel measurement and dilatation, the complexity of the device makes it difficult to fabricate with a sufficiently small diameter and sufficient flexibility for use in transluminal coronary angioplasty. In addition to the stiffness added by multiple electrodes, a separate conductor for each electrode passes through the catheter shaft.

Because of the requirement for accessing blood vessels of very small diameter, it has become commonplace in transluminal coronary angioplasty to use guidewires for controlling the placement of catheters. Catheters of sufficiently small diameter to be used in a small blood vessel typically lack the torsional rigidity to be adequately controlled as they are advanced through the vascular system to the obstructed site. Guidewires have an extremely small diameter, flexibility and sufficient torsional rigidity to be advanced to very small diameter blood vessels. The catheter is then advanced over the guidewire to the obstructed site. A steerable guidewire suitable for use in a balloon dilatation procedure is disclosed in U.S. Pat. No. 4,545,390 issued Oct. 8, 1985 to Leary and assigned to the assignee of the present application. The guidewire includes a small diameter, flexible rod having a distal region which is tapered. The tapered distal portion of the rod is surrounded by a helically-wound spring. The tip region of the guidewire is very flexible and can be bent to a predetermined shape which assists in guiding the device to an obstructed site. The guidewire disclosed in the Leary patent has no measurement capability.

A catheter including an intra-aortic balloon and a stylet normally used for twisting and untwisting the balloon is disclosed in U.S. Pat. No. 4,552,127, issued Nov. 12, 1985 to Schiff. An EKG electrode is affixed to the distal end of the stylet, and the stylet provides an electrical path from the EKG electrode to the proximal end of the catheter. A percutaneous lead that can be used for endocardial functions including mapping, ablation and pacing is disclosed in U.S. Pat. No. 4,660,571, issued Apr. 28, 1987 to Hess et al. In the Hess et al patent, a shaft utilized for torque control has an electrode at its distal end. The shaft functions as an electrical conductor from the electrode to the proximal end of the lead. An endocardial lead having a pair of spaced-apart, helically-wound electrodes on the outer surface of a flexible tube is disclosed in U.S. Pat. No. 4,481,953, issued Nov. 13, 1984 to Gold et al. A catheter for measuring blood flow including a pair of spaced-apart, helically-wound electrodes on the outer surface of a catheter tube is disclosed in U.S. Pat. No. 3,377,037, issued Nov. 20, 1973 to Kolin.

It is a general object of the present invention to provide a device for measuring the cross-sectional area of a blood vessel while avoiding the aforementioned problems.

It is another object of the present invention to provide improved methods and apparatus for measuring the cross-sectional area of a blood vessel and for measuring blood flow rate.

It is a further object of the present invention to provide a steerable guidewire having electrodes for measuring the cross-sectional area of a blood vessel and for measuring blood flow rate.

It is a further object of the present invention to provide a small diameter, steerable guidewire having a pair of spaced-apart electrodes near its distal end.

It is yet another object of the present invention to provide a small diameter, steerable guidewire having a highly flexible tip portion provided with a pair of spaced-apart electrodes.

SUMMARY OF THE INVENTION

According to the present invention, these and other objects and advantages are achieved in a steerable guidewire comprising an elongated shaft having a distal end and a proximal end, and a tip attached to the distal end of the shaft. The shaft is sufficiently torsionally rigid along its length for controllably transmitting to the distal end substantially all of the rotation applied to the proximal end. The shaft includes a first electrical conductor and a second electrical conductor electrically insulated from each other. The electrical conductors extend from the distal end to the proximal end of the shaft. The tip is adapted to be bent to a desired curve. The tip is sufficiently flexible to adapt to and follow the contours of a blood vessel. The tip includes a distal electrode electrically connected to the one of the conductors and a proximal electrode electrically connected to the other of the conductors. The electrodes are axially spaced apart on the tip by a predetermined distance.

In a preferred embodiment, the distal electrode and the proximal electrode each comprise a conductive, helically-wound spring. The first conductor comprises a conductive tube having a lumen therethrough, and the second conductor comprises a wire extending through the lumen in the tube. The wire and the tube are separated by an insulating layer. The tip includes a tapered distal region of the wire extending beyond the distal end of the tube. The tapered distal region passes through the proximal spring and at least a portion of the distal spring. The distal spring is electrically connected to the tapered distal region of the wire, and the proximal spring is electrically connected to the tube. The proximal spring and the distal spring are axially spaced apart by an insulating spacer.

Preferably, the shaft and the tip have a diameter that does not exceed about 0.020 inch. The proximal spring, the distal spring, the spacer and the tube have approximately equal outside diameters to provide a smooth outer surface for passage through the vascular system. In one preferred embodiment, the distal electrode is radiopaque to assist in fluoroscopic location of the measurement site.

Preferably, the steerable guidewire of the invention includes an insulating layer around the tube and around the proximal electrode, except for a portion of the proximal electrode adjacent to the spacer. In one preferred embodiment, the proximal spring is connected directly to the conductive tube. In this embodiment, the proximal spring is typically longer than the distal spring, and the springs are made of different materials to approximately equalize the resistances of the electrodes. In another embodiment, the proximal spring is spaced from the tube and is electrically connected thereto by a thin conductive ribbon. In this embodiment both springs are made from the same material.

According to another aspect of the present invention, there is provided a method for measuring blood flow rate in a blood vessel. The method comprises the steps of advancing an elongated, flexible member having a pair of spaced apart electrodes thereon through a blood vessel to a selected measurement site, sensing electrical current flow between the electrodes, injecting a biologically-safe liquid having a conductivity different from that of blood into the blood vessel upstream from the electrodes, sensing a change in current flow between the electrodes resulting from injection of the liquid, and determining blood flow rate from the change in current flow between the electrodes resulting from injection of the liquid. Preferably, the elongated, flexible member is a steerable guidewire having electrodes mounted near the distal end thereof as described above. The steerable guidewire is typically advanced so that the electrodes are positioned downstream of a stenosed region in the blood vessel, and the liquid is injected upstream of the stenosed region. The injected liquid is preferably a glucose solution.

BRIEF DESCRIPTION OF THE DRAWINGS

For a better understanding of the present invention together with other and further objects, advantages and capabilities thereof, reference is made to the accompanying drawings which are incorporated herein by reference and in which:

FIG. 1 illustrates a steerable guidewire system in accordance with the present invention;

FIG. 2A is an enlarged cross-sectional view of the steerable guidewire taken along the line 2A—2A of FIG. 1;

FIG. 2B is an enlarged cross-sectional view of the steerable guidewire taken along the line 2B—2B of FIG. 1;

FIG. 3 is a cross-sectional view of the guidewire shaft taken along the line 3—3 of FIG. 1;

FIG. 4 is an enlarged cross-sectional view of the distal end of the steerable guidewire in accordance with another embodiment of the invention.

DETAILED DESCRIPTION OF THE INVENTION

Figure 5:
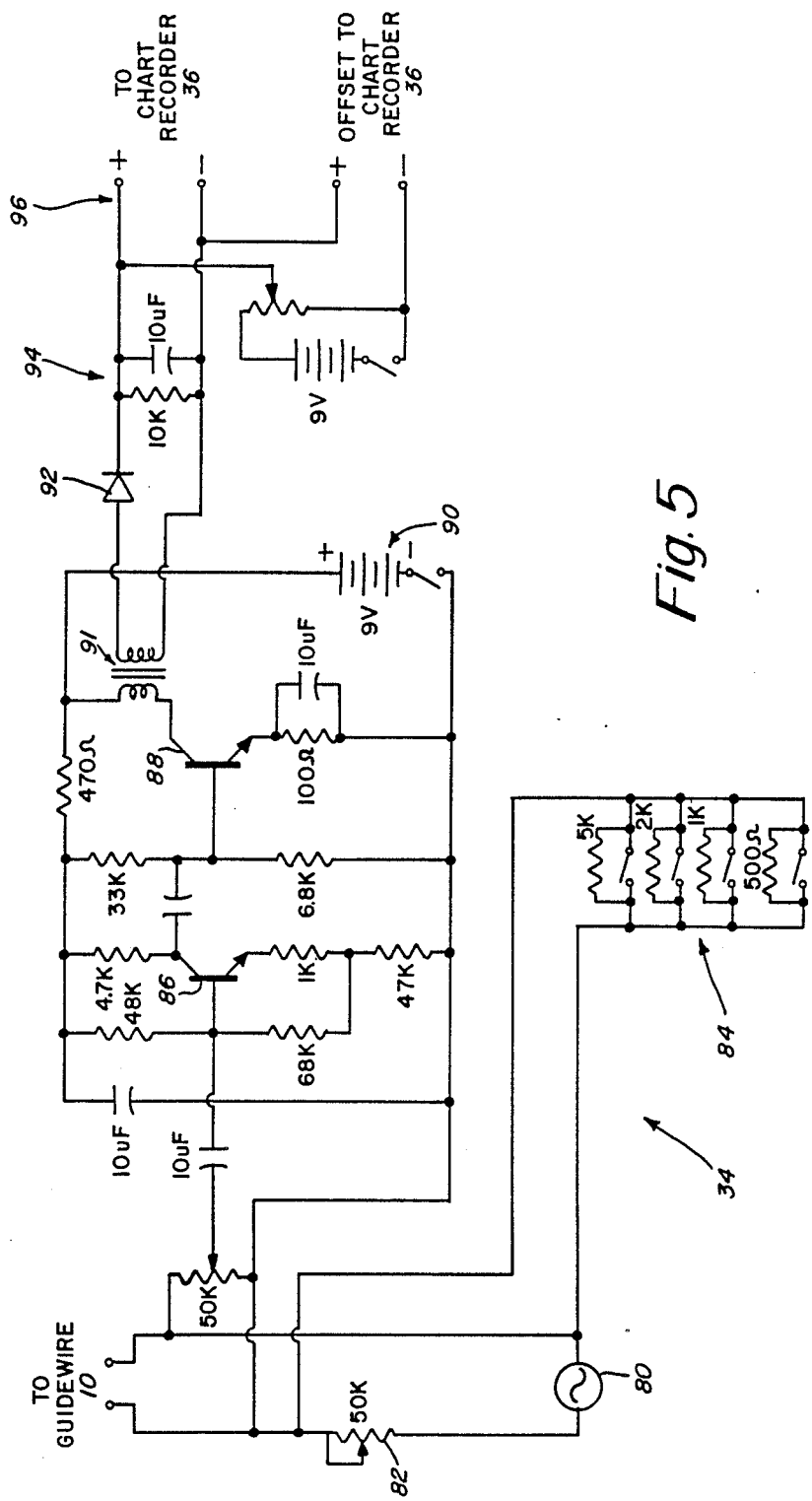
FIG. 5 is a schematic diagram of an excitation and sensing circuit suitable for use with the steerable guidewire.

A guidewire system including a steerable guidewire having electrodes for measuring vessel cross-section and coronary blood flow is shown in FIGS. 1–3. The guidewire has a very small diameter and is adapted to be controllably guided through the vascular system to the coronary region. The guidewire includes a pair of electrodes near its distal end that can be used for measuring the cross-sectional area of a blood vessel and for measuring coronary blood flow.

As shown in FIG. 1, a guidewire 10 includes an elongated shaft 12 having a distal end 12a and a proximal end 12b. The guidewire 10 also includes a distal tip region 14 coupled to the distal end 12a of shaft 12. The shaft 12, which may have a length on the order of 150 centimeters, is highly flexible but is torsionally rigid so that substantially all the rotation applied to the proximal end 12b is transmitted to the distal end 12a. The distal tip region 14, which may have a length on the order of 32 centimeters, can be bent to a predetermined, curved configuration when relaxed but is sufficiently flexible so as to adapt to and follow the contours of a blood vessel. Further details regarding the construction and use of steerable guidewires are provided in the aforementioned Pat. No. 4,545,390, which is hereby incorporated by reference.

The distal tip region 14 of guidewire 10 is provided with a distal electrode 20 and a proximal electrode 22 spaced apart by an insulating member 24. The distal electrode 20 and the proximal electrode 22 are electrically connected through shaft 12 by conductive wire 26 and conductive tube 28, respectively, to the proximal end of guidewire 10. Wire 26 and tube 28 are connected by leads 30 and 32, respectively, to an external excitation and sensing circuit 34. The excitation and sensing circuit 34 is connected to a chart recorder 36.

Conductive tube 28 is preferably a stainless steel tube, and wire 26 is an insulated core wire of stainless steel. In a preferred embodiment, tube 28 has a outside diameter of 0.016 inch and an inside diameter of 0.010-inch. The wire 26, which typically has a diameter of 0.008-inch, is electrically insulated from tube 28 by an insulating layer 40. The insulating layer 40, which is preferably a polyimide, can be a coating on wire 26 or can be a thin tube between wire 26 and tube 28.

Wire 26 includes a tapered distal portion 26a which extends beyond shaft 12 into the distal tip region 14. The proximal electrode 22 comprises a helically-wound, conductive spring coaxially mounted on the tapered portion 26a of wire 26. In the embodiment illustrated in FIGS. 2A and 2B, proximal spring 22 extends from the distal end 12a of shaft 12 to spacer 24. The proximal end of spring 22 abuts against and is electrically connected to the distal end of tube 28. The spring 22 can be silver-stainless steel having an outside coil diameter of 0.016-inch. The insulating member 24 is preferably a cylindrically-shaped spacer that is coaxially mounted on tapered portion 26a of wire 26 and abuts against the distal end of spring 22. The spacer 24, which typically has an axial length of two millimeters, establishes the spacing between electrodes 20 and 22. The axial length of spacer 24 should be small in order to obtain a localized measurement of cross-sectional area rather than an average value over an extended length.

The distal electrode 20 is a helically-wound, conductive spring that is coaxially mounted on tapered distal portion 26a and abuts against spacer 24. In a preferred embodiment, spring 20 is fabricated of platinum and has an axial length of 2.5 centimeters and an outside coil diameter of 0.016-inch. The distal spring 20 is electrically connected to wire 26, preferably by soldering or brazing, at a point about seven millimeters in a distal direction from spacer 24. The tapered portion 26a of wire 26 terminates within distal spring 20 at a point about 1.2 centimeters from spacer 24. A rounded bead 20a is formed at the distal end of spring 20, and a safety wire 42 is connected between bead 20a and tapered portion 26a. Insulating layer 40 covers the tapered portion 26a of wire 26 such that proximal electrode 22 is electrically insulated from wire 26 in the distal tip region.

In operation, an AC signal is applied to the electrodes 20 and 22 from circuit 34. A current flows through the blood between the spaced-apart electrodes 20 and 22. The current flow is related to the cross-sectional area of the blood vessel, as described more fully in the aforementioned Pat. No. 3,896,373.

In order to improve the sensitivity of the measurement, it is desirable to provide low electrical resistance through the guidewire to opposite sides of the spacer 24. The resistances of helical springs 20 and 22 are the major contributors to the total circuit resistance. Since proximal spring 22 is typically substantially longer than distal spring 20, the resistance of proximal spring 22 would be higher than the resistance of distal spring 20 if the same materials were used. In order to approximately equalize the resistances, different spring materials can be utilized. When the distal spring 20 is platinum and the proximal spring 22 is silver-stainless steel, the resistance of each electrodes is maintained below 200 ohms. A further advantage of the configuration where the distal electrode is platinum and the proximal electrode is silver-stainless steel is that the platinum electrode is radiopaque whereas the silver-stainless steel electrode is non-radiopaque. As a result, the measurement location at spacer 24 can clearly be identified by the physician using fluoroscopic techniques. If both electrodes were radiopaque, it would be more difficult to determine the exact location of spacer 24. It will be understood that different electrode materials can be utilized depending on the resistance requirements and the requirements for radiopaque electrodes. In cases where electrode resistance is not critical, platinum is preferably utilized for both electrodes because platinum has a lesser tendency to become oxidized or corroded than other metals.

The proximal end of wire 26 extends from tube 28 into a stainless steel tube 50. Tube 50 is spaced from tube 12 by an insulating spacer 52. Wire 26 is electrically connected to tube 50. Tube 50 and spacer 52 have the same diameter as the remainder of the guidewire to facilitate sliding a catheter over guidewire 10. Tube 50 remains external to the patient during use of the guidewire 10.

As described hereinabove, tubes 28 and 50 and helical springs 20 and 22 are all made of conductive material. In order to minimize leakage currents which would affect the accuracy of measurements made with the electrodes 20 and 22, it is desirable to provide an insulating layer 54 over the portions of these elements that are not used for making measurements. The entire length of the guidewire 10, except for exposed portions of electrodes 20 and 22 on either side of spacer 24, can be covered with insulating layer. Alternatively, since the distal electrode 20 is short in comparison with the remainder of the guidewire, the insulating layer can be omitted on distal electrode 20. Preferably, about two millimeters of each electrode 20, 22 is exposed adjacent to spacer 24. The insulating layer 54 can be formed as a coating on the outer surface of guidewire 10 or as a thin tube. A preferred material is polyimide. Preferably, the total outside diameter of the guidewire, including insulating layer 54, does not exceed about 0.020-inch. The guidewire shown in FIGS. 1-3 and described hereinabove can be fabricated in accordance with the following steps:

1. Barrel and taper grind a 0.008-inch × 70-inch stainless steel core wire 26.
2. Ultrasonically clean and oxidize (by plasma etch or baking) core wire 26.
3. Draw the core wire 26 through a dimethyl formamide/amide imide solution (Four parts to one respectively) at a rate of 24-inches per minute to form an insulating coating on core wire 26.
4. Cure the coated wire 26 in an oven for one hour at 300° C.
5. Insert the coated core wire 26 into a stainless steel tube 28 having an outside diameter of 0.016-inch and an inside diameter of 0.010-inch with 31 centimeters of the tapered portion of the core wire 26 outside of tube 28.
6. Bond insulated wire 26 to tube 28 with silver-filled epoxy or other cement.
7. Place proximal spring 22 over the core wire 26 and butt against tube 28. Then bond the spring 22 to the insulated core wire 26 and to tube 28 with silver-filled epoxy or solder.
8. Cure the epoxy in an oven for one hour at 150° C.

9. Place a two millimeter spacer (0.005-inch inside diameter by 0.016-inch outside diameter) over the end of the core wire and butt against proximal spring 22. Place distal spring 20 over the tapered core wire 26a and butt against spacer 24. Bond the ends of springs 20 and 22 to the core wire 26 and to spacer 24.
10. Push a six centimeter piece of stainless steel safety ribbon (0.001-inch×0.003-inch) into spring 20 until it stops.
11. Braze spring 20 to the safety ribbon 42 and core wire 26 at a point seven millimeters from the proximal end of spring 20.
12. Tip weld the distal end of spring 20.
13. Scrape off coating on core wire 26 at a point five millimeters from the proximal end of tube 28.
14. Slide a 5 millimeter long insulating spacer 52 (0.016-inch outside diameter×0.010-inch inside diameter) over the proximal end of core wire 26 and butt against the proximal end of tube 28.
15. Slide a 5 centimeter long tube 50 (0.016-inch outside diameter×0.010 inch inside diameter) over the proximal end of core wire 26 and butt against spacer 52.
16. Solder tube 50 to core wire 26 at the point where the coating was scraped off.

Another preferred embodiment of the steerable guidewire is shown in FIG. 4. The shaft portion of the guidewire is the same as the shaft of the guidewire shown in FIGS. 114 3 and described hereinabove. The shaft includes conductive tube 28 and wire 26 extending through tube 28. Tube 28 and wire 26 are insulated from each other. A distal tip region 70 includes a tapered distal portion 26a of wire 26. A proximal electrode 72 comprising a helically-wound, conductive spring is coaxially mounted on tapered distal portion 26a. The distal end of electrode 72 is spaced from the distal end of tube 28 by a distance on the order of 29 centimeters. Spacer 24 is coaxially mounted on tapered portion 26a of wire 26 abutting against proximal electrode 72, and distal electrode 20 is mounted on tapered portion 26a abutting against spacer 24. Distal electrode 20 is preferably a helically-wound platinum spring as described hereinabove. Since proximal electrode 72 is relatively short, it has approximately the same resistance as distal electrode 20 and is preferably platinum.

The proximal electrode 72 is electrically connected to tube 28 by a conductive ribbon 74. In a preferred embodiment, the conductive ribbon 74 is a platinum wire having dimensions of 0.001 inch×0.005-inch. The ribbon 74 is soldered or brazed to tube 28 at one end and to proximal electrode 72 at the other end. An insulating tube 76 surrounds a portion of the guidewire between the distal end of tube 28 and electrode 72. Preferably, tube 76 is fabricated of polyimide and extends from a point about two millimeters in a proximal direction from spacer 24 (thus exposing about two millimeters of electrode 72) to the proximal end of tube 28. The proximal electrode 72, by way of example, can have a length of about 10 millimeters. In the embodiment of FIG. 4, the overall length of the guidewire spring is relatively short.

In an alternative embodiment, the insulating tube 76 has a conductive coating or lining on its inside surface for electrically connecting tube 28 to proximal electrode 72. In this embodiment, ribbon 74 can be omitted.

A schematic diagram of the excitation and sensing circuit 34 is shown in FIG. 5. The output of a signal generator 80 is coupled through an amplitude adjustment circuit 82, 84 to leads 30 and 32. Leads 30 and 32 connect to wire 26 and tube 28, respectively, of the steerable guidewire 10 as shown in FIG. 1. Preferably, leads 30 and 32 are connected to tubes 50 and 28, respectively, by removable clips (not shown). Signal generator 80 is preferably a sinewave generator having a frequency of 50 KHz, an output amplitude of 0.25 volts peak-to-peak and a current of 10 microamps. The AC signal is applied between electrodes 20 and 22 of the guidewire causing electrical current to flow through the blood in the region of the vessel surrounding the spacer 24. The current flow varies with vessel cross-section adjacent to spacer 24. The voltage between leads 30 and 32 is sensed by an amplifier comprising transistors 86 and 88 and associated components. The amplifier is powered by a battery 90. The output of the amplifier is supplied through a transformer 91, a rectifier 92 and a low pass filter 94 to provide an output 96 to chart recorder 36. The output 96 is a DC voltage representative of the current flow between electrodes 20 and 22. The output 96 can be calibrated to provide readings of the cross-sectional area of the blood vessel. It will be understood that the circuit shown in FIG. 5 is given by way of example and is not in any way limiting.

The procedure for using the guidewire in accordance with the present invention involves placement and location of a conventional guide catheter so that its distal end is adjacent to the entry to the coronary artery. A dilatation catheter is prepared with the guidewire in place as described in the aforementioned Pat. No. 4,545,390. The guidewire extends through the main lumen of the dilatation catheter so that at about two centimeters of the distal tip of the guidewire project beyond the outlet of the dilatation catheter.

The assembly of dilatation catheter and guidewire is then pushed through the guide catheter into the coronary artery with the guidewire being used to manipulate dilatation catheter selectively into deeper and smaller coronary arteries. The simultaneous advancement of the dilatation catheter and guidewire is performed with the distal portion of the guidewire projecting distally beyond the outlet of the dilatation catheter. The projecting end of the guidewire tends to bias toward the curved configuration which the surgeon has preset. As the stenosis or obstruction is approached, the guidewire is advanced independently of the dilatation catheter in order to locate the guidewire with a high degree of precision with respect to the stenosis. The guidewire is advanced to the stenosed region by a combination of pushing and rotation or steering of its proximal end. The location of the guidewire can be verified fluoroscopically because of the highly radiopague characteristic of the distal spring 20.

When the electrodes 20 and 22 have been positioned in the stenosed region, a measurement of vessel cross-section is taken as described hereinabove. Then, the dilatation catheter is advanced over the guidewire until the balloon is located within the obstruction. The balloon is inflated to dilatate the stenosis and expand the vascular lumen. Balloon dilatation techniques are well known to those skilled in the art. After the dilatation procedure has been completed, the balloon catheter is withdrawn, at least partially, and the electrodes 20 and 22 are again positioned in the stenosed region. A second measurement of vessel cross-section is taken, thereby enabling verification of the effectiveness of the dilatation procedure. Thus, dilatation and measurement of very small vessels can be performed without removal of the balloon catheter and without insertion of a separate measuring device. The steerable guidewire of the present invention can be used in a manner similar to that described above with a laser catheter, a hot tip device or any other transluminal angioplasty device.

In accordance with another aspect of the procedure, the guidewire having electrodes 20 and 22 can be used for measuring blood flow through the stenosed region before and after the dilatation procedure. Blood flow is measured as follows. The guidewire is advanced to the stenosed region as described above and is positioned so that electrodes 20 and 22 pass through the stenosed region to the downstream side thereof. The dilatation catheter is advanced to the upstream side of the stenosed region, and a glucose solution is injected through the lumen of the dilatation catheter. Typically, about five milliliters of glucose solution is injected over a five second period. Initially, the electrodes sense the cross sectional area of the vessel by conduction through blood. When the glucose solution is injected into the vessel, it passes through the stenosed region to the electrodes, causing a reduction in current flow between electrodes. Depending on the extent to which blood is flowing in the vessel, higher or lower concentrations of glucose solution reach the electrodes. Thus, the drop in current between electrodes 20 and 22 as the glucose solution is injected is a measure of the blood flow in the vessel.

The change in current appears as a variation or curve on the chart recorder 36 or other recording device. After the glucose solution dissipates, the measured current between electrodes 20 and 22 returns to its original value. Blood flow is determined as a function of the area under the chart recorder curve during glucose flow in accordance with the Stewart-Hamilton equation:

$$Q = \frac{kI}{A}$$

where
Q = Rate of blood flow,
A = Area under curve in ohm-sec,
I = Volume of injected glucose solution, and
k = Constant in ohms.

A flow measurement can be obtained before and after the balloon dilatation procedure to provide an indication of the effectiveness of the dilatation procedure. It will be understood that the above-described method can also be used to measure blood flow in a vessel that is not stenosed.

While there have been shown and described what are at present considered the preferred embodiments of the present invention, it will be obvious to those skilled in the art that various changes and modifications may be made therein without departing from the scope of the invention as defined by the appended claims.

What is claimed is:

1. A steerable guidewire comprising:
an elongated shaft having a distal end and a proximal end, said shaft being sufficiently torsionally rigid along its length for controllably transmitting to the distal end substantially all of the rotation applied to the proximal end, said shaft including a first electrical conductor and a second electrical conductor insulated from said first electrical conductor, said electrical conductors extending from the distal end to the proximal end of said shaft; and
a tip attached to the distal end of said shaft, said tip adapted to be bent to a desired curve, said tip being sufficiently flexible so as to adapt to and follow the contours of a blood vessel, said tip including a distal electrode electrically connected to one of said conductors and a proximal electrode electrically connected to the other of said conductors, said electrodes being axially spaced apart on said tip by a predetermined distance, said distal electrode comprising a distal, conductive, helically-wound spring and said proximal electrode comprising a proximal, conductive helically-wound spring, said tip including a tapered distal region of said second conductor passing through said proximal spring at and least a portion of said distal spring and electrically connected to said distal spring.

2. A steerable guidewire as defined in claim 1 wherein said shaft and said tip have a diameter that does not exceed about 0.020-inch.

3. A steerable guidewire as defined in claim 1 wherein said first conductor comprises a main conductive tube having a lumen therethrough.

4. A steerable guidewire as defined in claim 3 wherein said second conductor comprises a wire extending through the lumen in said tube.

5. A steerable guidewire as defined in claim 1 wherein said tube includes a distal end and wherein said tapered distal region of said second conductor includes a tapered distal region of said wire extending beyond the distal end of said tube, said tapered distal region of said wire passing through said proximal spring and at least a portion of said distal spring.

6. A steerable guidewire as defined in claim 5 wherein a distal spring is electrically connected to the tapered distal region of said wire.

7. A steerable guidewire as defined in claim 6 wherein said proximal spring is electrically connected to said tube.

8. A steerable guidewire as defined in claim 7 wherein said proximal spring and said distal spring are axially spaced apart by a cylindrical insulating spacer on said wire.

9. A steerable guidewire as defined in claim 7 wherein said proximal spring, said distal spring and said spacer have approximately equal outside diameters.

10. A steerable guidewire as defined in claim 8 further including an insulating layer around said tube and said proximal electrode except for a portion of said proximal electrode adjacent to said spacer.

11. A steerable guidewire as defined in claim 10 wherein said insulating layer comprises a polyimide sleeve.

12. A steerable guidewire as defined in claim 8 wherein said spacer has an axial length of about 2 millimeters.

13. A steerable guidewire as defined in claim 6 wherein said proximal spring is spaced from the distal end of said tube and is electrically connected thereto by a conductive ribbon.

14. A steerable guidewire as defined in claim 4 wherein said wire is insulated from said tube by an insulating coating on said wire.

15. A steerable guidewire as defined in claim 4 wherein said wire is insulated from said tube by a polyimide sleeve on said wire.

16. A steerable guidewire as defined in claim 4 further including a proximal conductive tube proximally spaced from said main tube and electrically connected to said wire.

17. A steerable guidewire as defined in claim 4 wherein said tube as an outside diameter of about 0.016-inch, and said wire has an outside diameter of about 0.008-inch.

18. A steerable guidewire as defined in claim 1 wherein said distal electrode is radiopaque.

19. A steerable guidewire as defined in claim 1 wherein said electrodes are axially spaced apart by a distance that is sufficiently small to provide highly localized measurements.

20. A small diameter steerable guidewire comprising;
a main conductive tube having a proximal end and a distal end;
a conductive wire extending through said tube and having a tapered distal region extending beyond the distal end of said tube, said wire being electrically insulated from said tube;
a distal, conductive, helically-wound spring receiving at least a portion of the distal region of said wire, said distal spring constituting a distal electrode and being electrically connected to said wire;
a proximal, conductive, helically-wound spring having the distal region of said wire extending therethrough, said proximal spring constituting a proximal electrode and being electrically connected to said tube; and
means for spacing said distal and proximal electrodes by a predetermined distance on the distal region of said wire.

21. A steerable guidewire as defined in claim 20 wherein said proximal spring is connected directly to said tube.

22. A steerable guidewire as defined in claim 21 wherein said proximal spring and said distal spring are coaxial with said wire.

23. A steerable guidewire as defined in claim 23 wherein the materials of said proximal electrode and said distal electrode are selected to approximately equalize the electrical resistances of the electrodes.

24. A steerable guidewire as defined in claim 23 wherein said proximal electrode is longer than said distal electrode, wherein said proximal electrode is fabricated of silver stainless steel and wherein said distal electrode is fabricated of platinum.

25. A steerable guidewire as defined in claim 20 wherein each electrode is fabricated of platinum.

26. A steerable guidewire as defined in claim 20 wherein said distal electrode is radiopaque.

27. A steerable guidewire as defined in claim 20 wherein said spacing means comprises a cylindrical insulating spacer having an outside diameter approximately equal to the outside diameters of said proximal and distal electrodes.

28. A steerable guidewire as defined in claim 20 wherein said tube, said proximal electrode and said distal electrode each have an outside diameter of about 0.020-inch or less.

29. A steerable guidewire as defined in claim 20 further including an insulating layer around said tube and said proximal electrode except for a portion of said proximal electrode adjacent to said spacing means.

30. A steerable guidewire as defined in claim 31 wherein said insulating layer comprises a polyimide tube.

31. A steerable guidewire as defined in claim 29 wherein said insulating layer comprises an insulating tube.

32. A steerable guidewire as defined in claim 20 wherein said tube is insulated from said wire by an insulating coating on said wire.

33. A steerable guidewire as defined in claim 20 wherein said tube is insulated from said wire by a polyimide sleeve on said wire.

34. A steerable guidewire as defined in claim 20 wherein said tube, said proximal electrode and said distal electrode have approximately the same outside diameters.

35. A steerable guidewire as defined in claim 20 further including a proximal conductive tube proximally spaced from said main tube and coaxial with said wire, said proximal tube being electrically connected to said wire.

36. A steerable guidewire as defined in claim 20 wherein said tube has an outside diameter of about 0.016-inch, and said wire has an outside diameter of about 0.008 inch.

37. A steerable guidewire as defined in claim 20 wherein said proximal electrode is spaced from the distal end of said tube and is electrically connected thereto by a conductive ribbon.

38. A steerable guidewire as defined in claim 37 wherein a region between the distal end of said tube and said proximal electrode is covered with a insulating tube.

39. A steerable guidewire as defined in claim 37 wherein said main conductive tube, said distal and proximal springs and said means for spacing each have an outside diameter not greater than about 0.020-inch.

40. A steerable guidewire as defined in claim 20 wherein said proximal electrode is spaced from the distal end of said tube, wherein a region between the distal end of said tube and said proximal electrode is covered with an insulating tube and wherein said proximal electrode is electrically connected to said tube.

* * * * *